(12) United States Patent
Ishida (10) Patent No.: US 6,299,605 B1
(45) Date of Patent: *Oct. 9, 2001

(54) PACK FOR THE NOSE (75) Inventor: Koichi Ishida, Tokyo (JP)

(73) Assignee: Kao Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/091,843

(22) PCT Filed: Oct. 24, 1997

(86) PCT No.: PCT/JP97/03877

§ 371 Date: Jul. 1, 1998

§ 102(e) Date: Jul. 1, 1998

(87) PCT Pub. No.: WO98/19643

PCT Pub. Date: May 14, 1998

(30) Foreign Application Priority Data

Nov. 5, 1996 (JP) .................................................. 8-011906

(51) Int. Cl.[7] .......................... A61M 35/00; A61F 13/02; A45D 40/26; F16B 2/00
(52) U.S. Cl. .......................... 604/289; 604/307; 132/320; 424/443; 428/33; 514/844; 514/848
(58) Field of Search ............................. 607/109; 602/41, 602/74, 17, 900, 902–903; 128/858, 848, 207.18, 888–894; 2/26, 53–58, 206; 604/289, 303, 304, 307, 308, 313; 606/199; 428/33; 283/87; 517/21, 844, 848; 132/319, 320; 424/445, 443, 447–448

(56) References Cited

U.S. PATENT DOCUMENTS

| D. 388,533 | | 12/1997 | Uemura et al. . |
| D. 388,534 | | 12/1997 | Uemura et al. . |
| 766,963 | * | 8/1904 | Murray . |
| 1,291,846 | * | 1/1919 | Greenfield . |

(List continued on next page.)

FOREIGN PATENT DOCUMENTS

| 60/165902 | 8/1985 | (JP) . |
| 61/23916 | 2/1986 | (JP) . |
| 6/4032 | 6/1992 | (JP) . |

(List continued on next page.)

OTHER PUBLICATIONS

Examination Reports Feb. 26, 1998 and Oct. 20, 1999 for GB 9722933.0.
Office Action Mar. 26, 1999 for Taiwanese Application 86116075.
Notice of Preliminary Rejection Jun. 29, 1999 for Korean Application 10–1997–0058088.

Primary Examiner—Dennis Ruhl
Assistant Examiner—K. M. Reichle
(74) Attorney, Agent, or Firm—Oblon, Spivak, McClelland, Maier & Neustadt, P.C.

(57) ABSTRACT

A sheet-like pack 1A for the nose, being applicable to the skin of the nose, comprises a holding member 20 and a cosmetic material 30, and a receding portion 6 is formed at the middle of an upper edge 2 of the pack and a projecting portion 5 is formed at the middle of a lower edge 3 of the pack. These receding portions 6 and projecting portion 5 have shapes which are fittable with each other. This provides a pack for the nose which can readily fit with the nose of various shapes, inclusive of the tip of the nose, and can contribute to an improvement in yield when manufactured in a conveyor system. This also provides for a method of forming a pack and a sheet comprising packs.

11 Claims, 5 Drawing Sheets

U.S. PATENT DOCUMENTS

| | | | |
|---|---|---|---|
| 2,001,862 | * | 5/1935 | Battey .................................. 604/307 |
| 2,438,771 | * | 3/1948 | Topjian . |
| 3,259,911 | * | 7/1966 | Tyrell, Jr. . |
| 4,631,227 | * | 12/1986 | Nakamura ............................ 604/289 |
| 4,719,909 | * | 1/1988 | Machia et al. ....................... 128/888 |
| 5,221,382 | * | 4/2001 | Ishida et al. . |
| 5,407,685 | * | 4/1995 | Malchesky et al. . |
| 5,512,277 | | 4/1996 | Uemura et al. . |
| 6,042,844 | * | 3/2000 | Ishida et al. . |
| 6,221,382 | * | 4/2001 | Ishida et al. . |

FOREIGN PATENT DOCUMENTS

| | | |
|---|---|---|
| 8/169809 | 7/1996 | (JP) . |
| 8-011906 | 7/1997 | (JP) . |
| WO 97/32567 | 12/1997 | (WO) . |

\* cited by examiner

PACK FOR THE NOSE

TECHNICAL FIELD

This invention relates to a pack for the nose, which is a sheet-like pack of a peel-off type, has upper and lower edges having shapes which are fittable with each other, and can contribute to an improvement in yield when manufactured. More particularly, it relates to a pack for the nose which is suitable as a pack for pores of the skin, used to remove keratotic plugs of the nose skin.

BACKGROUND ART

Peel-off type sheet-like packs are cosmetic materials of the type that the pack is stuck on the surface of the skin with its film-forming cosmetic material surface in contact and, after it has been left to stand for a certain time until a film is formed, the film is peeled from the skin. Such peel-off type sheet-like packs, depending on the constituents of cosmetic materials used there, commonly impart moisture content, moistening components or the like to stratum corneum when used and absorb sebum secreted from the skin. They also impart an appropriate tenseness to the skin by the formation of film to improve blood circulation. They still also remove dirt, keratotic plugs and so forth of the skin when peeled. Hence, peel-off type packs are important for achieving a high emollient effect and a high rinsing effect. In particular, much sebum is secreted from pores of the nose skin, and the sebum may mix with stratum coneum to form keratotic plugs, so that the pores of the skin may extend, the surface of the skin may feel rough or the tops of keratotic plugs may blacken to damage the beauty of the skin, thus the peel-off type packs are useful for the nose.

Peel-off type packs are hitherto known as jelly, pasty and powdery products. Of these, jelly products and pasty products are applied to the skin as they are, and films having been thus formed are peeled. Powdery products are turned liquid by previously adding a liquid such as water, and the liquid formed is applied to the skin, and films having been thus formed are peeled.

When these are used, however, cosmetic materials constituting a pack are applied to the skin with fingers, and hence unnecessary cosmetic materials adhere to the fingers when applied, thus there is a problem that the cosmetic materials are wasted and also the fingers become dirty. There is another a problem that the cosmetic materials can not be uniformly applied to the skin surface. Also, since the cosmetic materials must be left to stand for a long time after they are applied to the skin and until the formation of a film is completed, there is still another problem that the packs are troublesome to use. Moreover, the film may have an insufficient film strength when the materials are used in a usual amount, and there is a further problem that the film may be torn off when peeled, to remain unpeeled on the skin surface.

Accordingly, in recent years, sheet-like packs comprising a holding member such as nonwoven fabric, and a film-forming cosmetic material previously coated thereon have been proposed, and put on the market.

As forms of such sheet-like packs, some of them are provided for users in the form of rectangular sheets so that individual users may cut a rectangular sheet into desired shapes when used, in accordance with the portions to be packed, and some of them are previously shaped to have outer shapes fittable with the portions to be packed. Of these, a sheet-like pack shaped as a pack for the nose is known to include, e.g., the one as shown in FIGS. 12A and 12B.

Figure 12A:
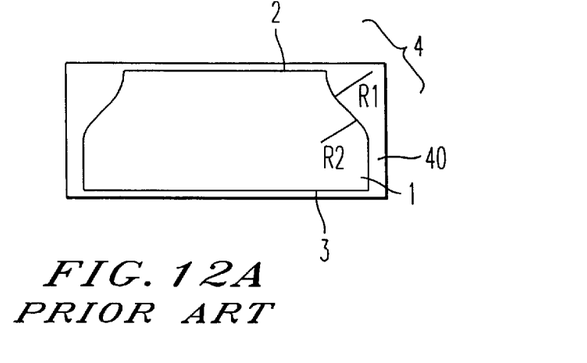
FIGS. 12A and 12B are a plan view (FIG. 12A) of a conventional pack for the nose and a view (FIG. 12B) to illustrate how it stands when applied to the nose.

The pack for the nose denoted by reference numeral 1 in FIG. 12A has an upper edge 2 and a lower edge 3 which are formed in straight lines parallel to each other, and has a substantially trapezoidal outer shape. The sides between the upper edge 2 and the lower edge 3 form curves. In particular, their shoulders 4 each form a continuous curve consisting of an arc (curvature radius: R1) curved inward and an arc (curvature radius: R2) curved outward. Also, this pack 1 for the nose is held on a release film 40 before its use.

Figure 12B:
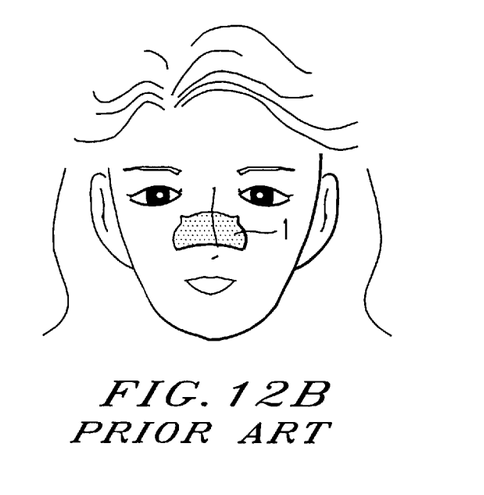

FIG. 12B illustrates how this pack 1 for the nose is actually applied on the nose. As shown in the drawing, use of this pack 1 for the nose makes it possible to well cover almost the whole nose in the state the pack adheres closely to the skin of the nose, compared with an instance where a merely rectangular sheet-like pack is used.

Figure 13A:
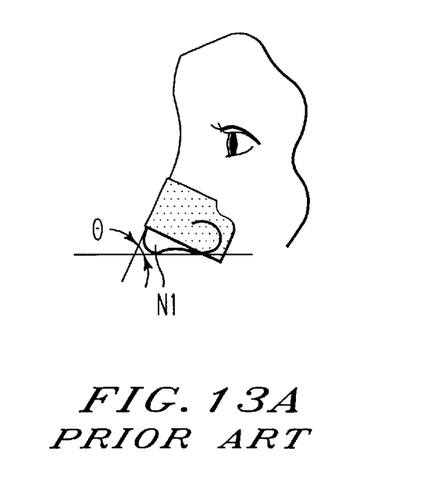
FIGS. 13A and 13B illustrates what are problems when a conventional pack for the nose is applied to the nose.
Figure 13B:
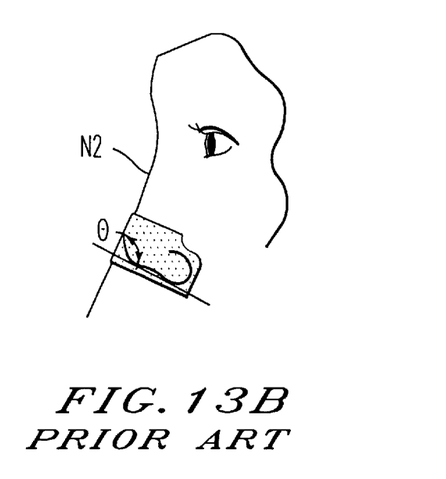

However, each has one's own shape of the nose such as one's own height, width and angle of the nose, which may greatly differ from one another. Hence, even if the pack 1 for the nose as shown in FIGS. 12A and 12B is used, the pack can not be applied to some part of the nose, depending on the shape of the nose. For example, as shown in FIG. 13A, the tip N1 of the nose tends to protrude from the pack 1 when one has a prominent nose and the nose has an acute angle θ. On the other hand, as shown in FIG. 13B, the ridge N2 of the nose (dorsum nasi) can not be widely covered when one has a flat nose and the nose has an obtuse angle θ.

Figure 9:
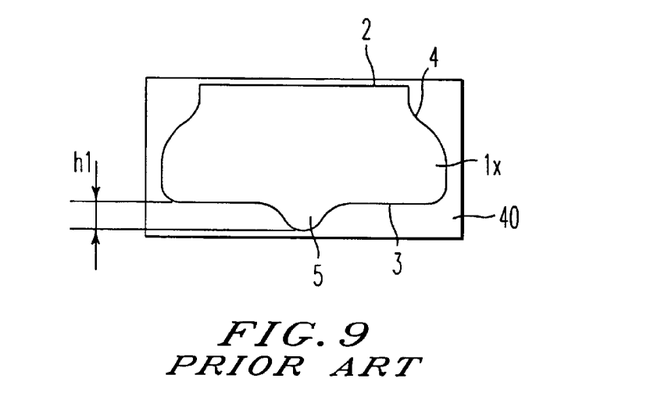
FIG. 9 is a plan view of a conventional pack for the nose, provided with a projecting portion at the middle of its lower edge.

To cope with such problems, one may contemplate to provide, like a pack 1x for the nose as shown in FIG. 9, a projecting portion 5 at a lower edge 3 so that the tip of the nose can be covered when the pack is applied and the tip of the nose can be surely covered however various shapes the nose may have.

Figure 10:
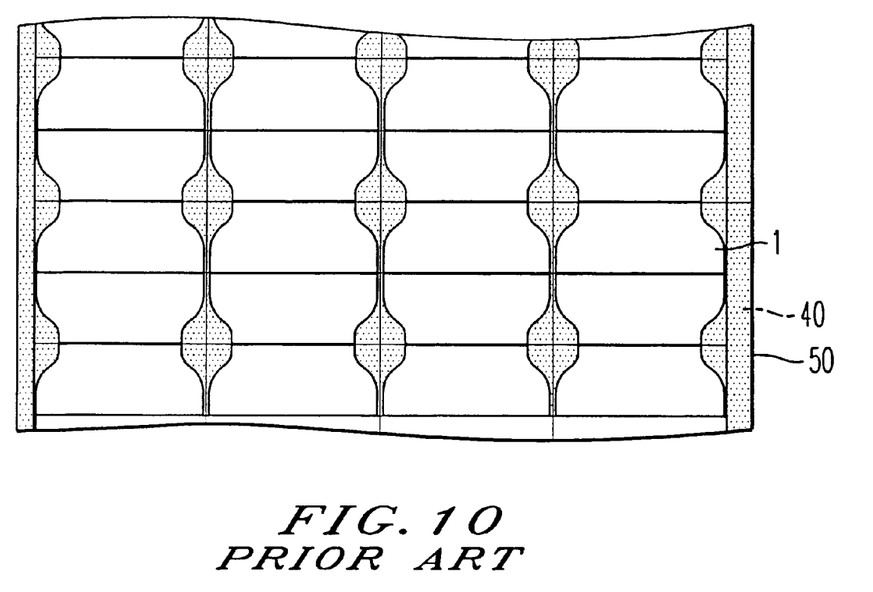
FIG. 10 illustrates how conventional packs for the nose are cut out of a raw sheet.
Figure 11:
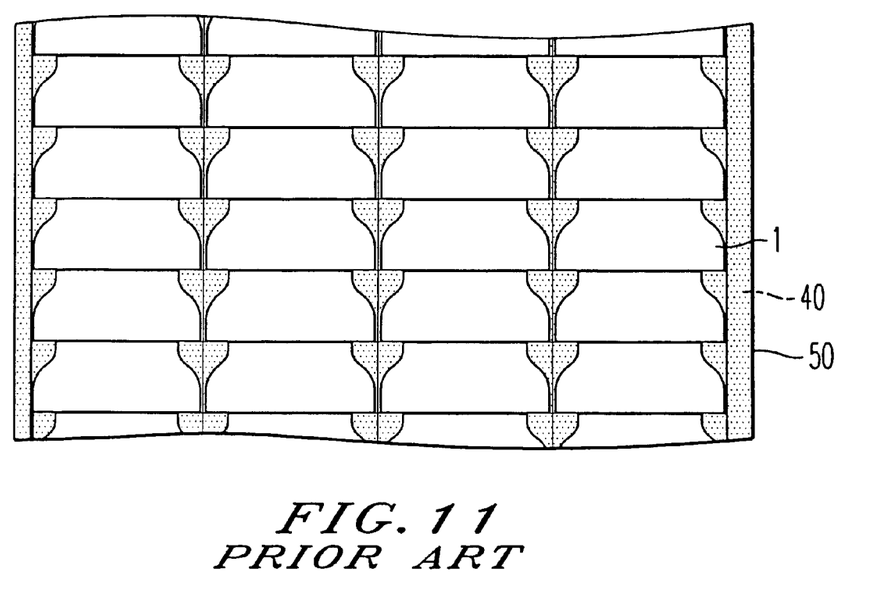
FIG. 11 illustrates how conventional packs for the nose are cut out of a raw sheet.

However, when the projecting portion 5 is provided at the lower edge 3 as in the pack 1x for the nose as shown in FIG. 9, a problem occurs such that its manufacture results in a low yield on production lines compared with the FIG. 12A pack 1 for the nose. More specifically, when the conventional pack 1 for the nose as shown in FIG. 12A is manufactured in a conveyor system, as shown in FIG. 11 a plurality of packs 1 for the nose are continuously cut out of a raw sheet 50 of the packs for the nose, laminated onto a wide release film 40. In this instance, in the state the upper edge 2 of any one pack 1 for the nose and the lower edge 3 of other adjacent pack 1 for the nose are set closely face-to-face, the raw sheet 50 is first half-cut and then the portions not used as the pack 1 for the nose (the areas dotted out in the drawing) are peeled off. Thereafter, the whole is cut into individual forms of products on the release film 40 of which each pack 1 for the nose is held. Alternatively, as shown in FIG. 10, the packs 1 for the nose are continuously cut out in the state their upper edges 2 and lower edges 3 of mutually adjacent packs 1 for the nose are respectively set face-to-face.

Figure 7:
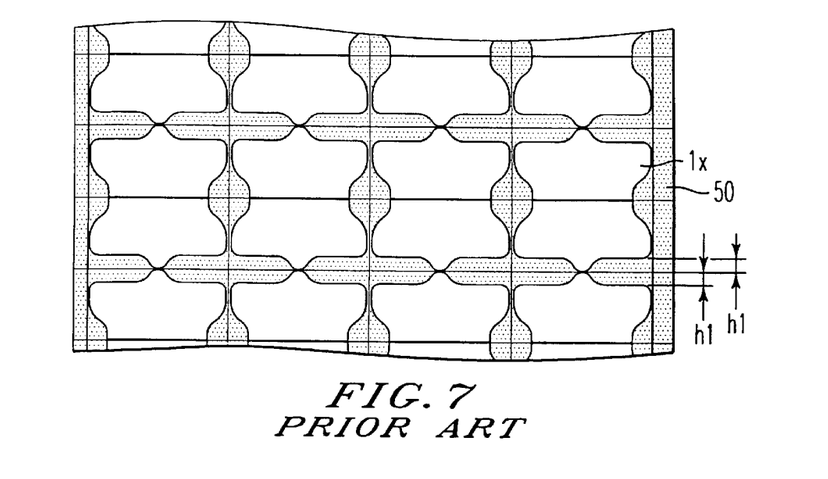
FIG. 7 illustrates how conventional packs for the nose are cut out of a raw sheet; each pack having a projecting portion at the middle of its lower edge.
Figure 8:
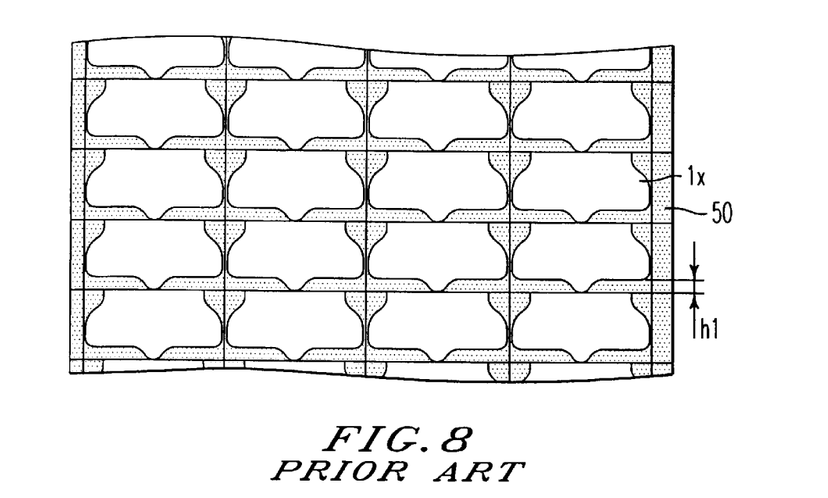
FIG. 8 illustrates how conventional packs for the nose are cut out of a raw sheet; each pack having a projecting portion at the middle of its lower edge.

In contrast, when the pack 1x for the nose as shown in FIG. 9, provided with the projecting portion 5, is similarly manufactured in a conveyor system, a plurality of packs 1x for the nose are cut out in the state they are arranged in the same direction as shown in FIG. 8, or they are cut out in the state their upper edges 2 and lower edges 3 of mutually adjacent packs 1x for the nose are respectively set face-to-face as shown in FIG. 7. Here, when cut in the manner as shown in FIG. 8, it follows that a space corresponding to a height h1 of the projecting portion 5 provided at the lower edge 3 is left between the upper edge 2 of one pack 1x for the nose and the lower edge 3 of other adjacent pack 1x for the nose. Thus, the upper edge 2 of one pack 1x for the nose can not be brought into close contact with the lower edge 3 of other adjacent pack 1x for the nose, which can be done when cut in the manner as shown in FIG. 11. Also when cut in the manner as shown in FIG. 7, because of a height h1 of the projecting portion 5 provided at the lower edge 3, it follows that a large space is left between upper edges 2 and between shoulders 4 of mutually adjacent packs 1x for the nose, so that these can not be brought into close contact. In addition, in the both cases of FIG. 7 and FIG. 8, when the areas dotted out are peeled off, a space must be kept between the mutually adjacent packs 1x for the nose in order to make it possible to continuously peel off the dotted-out areas in the state they link one another. In such an instance, however, the space between the mutually adjacent packs 1x for the nose must be made larger. Accordingly, in the case of this pack 1x for the nose, the portions not used as the pack 1x for the nose are held in a high proportion in the raw sheet (percentage of disposal of raw sheets), causing the problem of a low yield of products.

DISCLOSURE OF THE INVENTION

The present invention will solve the above problems the prior art involves. Accordingly, an object of the present invention is to provide a pack for the nose which can readily fit with the nose of various shapes and can contribute to an improvement in yield when manufactured in a conveyor system.

To achieve the above object, the present invention provides a sheet-like pack for the nose, comprising a holding member and a cosmetic material and being applicable to the skin of the nose; wherein a receding portion is formed at the middle of an upper edge of the pack and a projecting portion is formed at the middle of a lower edge of the pack; the receding portion and projecting portion having shapes which are fittable with each other.

According to the pack for the nose of the present invention, a projecting portion is formed at the middle of a lower edge of the pack, and hence the pack can widely cover the nose of various shapes, inclusive of the tip of the nose. Also, a receding portion having a shape fittable to the shape of the projecting portion at the lower edge is formed at the upper edge. Hence, when packs for the nose are cut out of raw sheets on production lines, they can be cut out in such a state that the upper edge of one pack for the nose is fitted with the lower edge of other adjacent pack for the nose. Thus, the raw sheet can be used at a low percentage of disposal, bringing about an improvement in yield of products.

In the pack for the nose of the present invention, there are no particular limitations on its layer configuration and constituent materials. For example, the holding member may comprise a moisture-impermeable filmy base material and the cosmetic material may be laminated to its one surface as an adhesive layer to form a tape type product, or the holding member may comprise a moisture-permeable sheet-like base material such as nonwoven fabric and may be impregnated with the cosmetic material, or the cosmetic material may be laminated to the base material so as to be held thereon. In particular, from the viewpoint of promoting the film formation of the cosmetic material, the holding member may preferably be moisture-permeable. Accordingly, the present invention provides an embodiment in which, in the above pack for the nose, the holding member is moisture-permeable.

The present invention also provides, as an embodiment preferred in view of layer configuration and constituent materials, an embodiment in which the moisture-permeable holding member comprises a multi-layer type moisture-permeable holding member having a water-repellent layer and a hydrophilic layer, where the cosmetic material is held in at least the hydrophilic layer and the water-repellent layer forms one surface of the sheet-like pack. In particular, it provides an embodiment in which the cosmetic material is a keratotic plug removable cosmetic material containing a polymeric compound having a salt-forming group selected from a carboxyl group, a sulfonic acid residual group, a sulfuric acid residual group, a phosphoric acid residual group, a nitric acid residual group, an amino group and an ammonium group; in particular, an embodiment in which the keratotic plug removable cosmetic material comprises polymethacryloyloxyethyltrimethylammonium chloride.

BEST MODE FOR WORKING THE INVENTION

The present invention will be described below in detail with reference to the drawings. In the drawings, like reference numerals denote like or equivalent constituents.

Figure 1A:
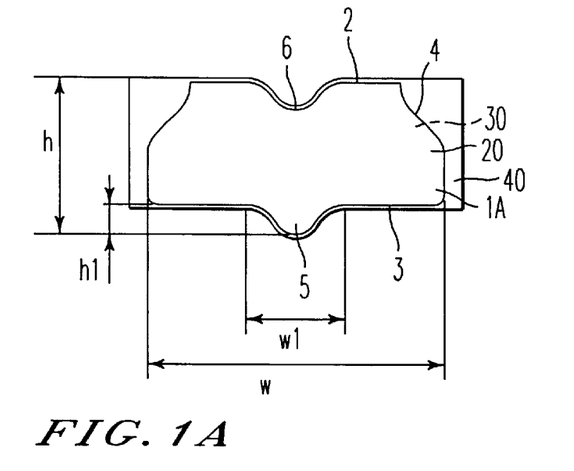
FIGS. 1A and 1B are a plan view (FIG. 1A) and a partial cross-sectional view (FIG. 1B), of the pack for the nose according to the present invention.
Figure 1B:
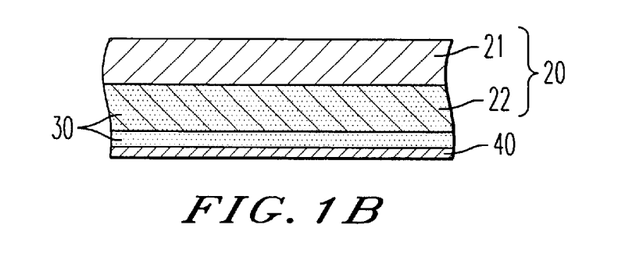
Figure 2:
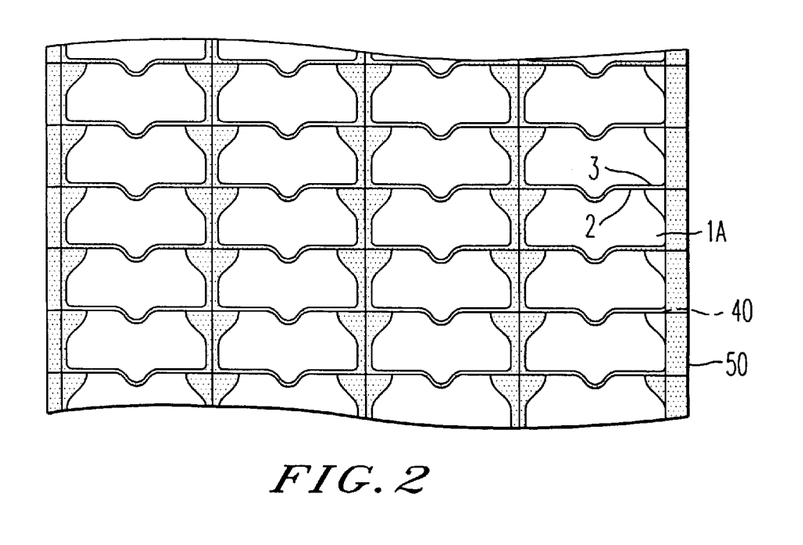
FIG. 2 illustrates how packs for the nose according to the present invention are cut out of a raw sheet.

FIGS. 1A and 1B are a plan view (FIG. 1A) of a pack 1A for the nose according to the present invention and a cross-sectional view (FIG. 1B) thereof.

This pack 1A for the nose comprises a moisture-permeable holding member 20 formed of a nonwoven fabric of double-layer structure comprised of a water-repellent layer 21 and a hydrophilic layer 22, and a cosmetic material 30 held in the hydrophilic layer 22 of the moisture-permeable holding member 20 and also present as a sole layer on the hydrophilic layer 22. A release film 40 is provided on the surface of the cosmetic material 30.

While the conventional pack 1 for the nose as shown in FIGS. 12A and 12B has the upper edge 2 and the lower edge 3 each of which forms a straight line, the present pack 1A for the nose is characterized in that a projecting portion 5 is formed at the middle of its lower edge 3, a receding portion 6 is formed at the middle of an upper edge of the pack, and the projecting portion 5 and receding portion 6 have shapes which are fittable with each other.

That is, in the present pack 1A for the nose, the projecting portion 5 is formed at the middle of a lower edge 3 of the pack. Hence, it becomes possible to widely cover the nose, inclusive of the tip N1 of the nose, even if the nose has an acute angle θ as shown in FIG. 13A. In this instance, the shape and size of the projecting portion 5 may be appropriately determined according to height h, with w and so forth of the pack 1A. For example, when the pack has a height h of about 30 to 50 mm, the projecting portion may preferably have an outer shape with a width w1 of 5 to 50 mm and a height h1 of from 3 to 30 mm, and may preferably be formed of an arc having a curvature radius of about 3 to 40 mm, preferably 3 to 40 mm.

Meanwhile, the receding portion 6 formed at the upper edge has a shape fittable to the shape of the projecting portion 5 of the lower edge. Hence, when the pack 1A for the nose is manufactured in a conveyor system, a plurality of packs 1A for the nose can be continuously cut out of the raw sheet 50 laminated onto a wide release film 40. In this instance, the packs are cut out in the state the upper edge 2 of one pack 1A for the nose and the lower edge 3 of other adjacent pack 1A for the nose are set closely face-to-face. The space corresponding to a height hl of the projecting portion 5 as in the case when the packs 1x for the nose, having no receding portion 6 at the upper edge 2 as shown in FIG. 8, are cut out is not left between the upper edge 2 of one pack 1A for the nose and the lower edge 3 of other adjacent pack 1A for the nose. Thus, it becomes possible to use the raw sheet at a low percentage of disposal and to improve the yield of products.

The receding portion 6 at the middle of the upper edge 2 not only contributes to an improvement in yield on production lines of the pack 1A for the nose in this way, but also makes it easy to make registration of the receding portion 6 to the route of the nose when the pack 1A is stuck to the nose. Hence, this pack 1A for the nose makes it possible to apply the pack to the nose in its optimum proper position without being right and left out of position.

The pack 1A for the nose as shown in FIGS. 1A and 1B has a substantially trapezoidal outer shape, having shoulders 4 formed of curves, in the same manner as in FIG. 9 except that it has the projecting portion 5 at the lower edge and the receding portion 6 having a shape fittable thereto at the upper edge.

Figure 3:
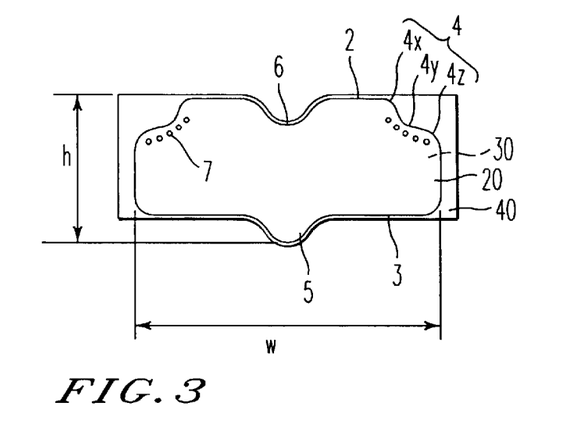
FIG. 3 is a plan view of the pack for the nose according to the present invention.

So long as the receding portion 6 and projecting portion 5 having shapes fittable with each other are formed at the upper edge 2 and the lower edge 3, respectively, as described above, the pack for the nose according to the present invention may have various outer shapes. For example, as shown in FIG. 3, shoulders 4 may be formed of a continuous curve consisting of a projecting portion 4x, a recessed portion 4y and a projecting portion 4z successively from the upper edge 2 side toward the lower edge 3 side so that the air present between the pack and the skin can be easily put out to improve the adhesion of the pack by moving fingers from the top of the ridge of the nose toward the shoulders 4 of the pack while pressing the pack with the fingers when the pack is applied. In this instance, the curvature radii of the curves that form these projecting portions and a recessed portion may be appropriately determined depending on the pack area covering the nose, an appearance and so forth. For example, when the pack 1A for the nose has a height h of from 30 to 40 mm and a width w of from 70 to 90 mm, the arc that forms the projecting portion 4x on the upper edge side may be in a curvature radius of from 1 mm to 20 mm, the arc that forms the recessed portion 4y may be in a curvature radius of from 5 mm to 50 mm, and the arc that forms the projecting portion 4z on the lower edge side may be in a curvature radius of from 5 mm to 50 mm. Here, these arcs may preferably be made smoothly continuous in view of appearance.

Air vent holes 7 may be further formed in the vicinity of each shoulder 4 so that the air present between the pack and the skin when the pack is applied can be more easily put out to improve the adhesion of the pack.

Figure 4:
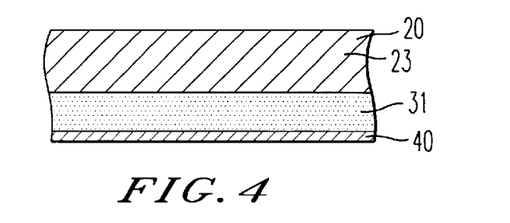
FIG. 4 is a partial cross-sectional view of the pack for the nose according to the present invention.

The pack for the nose according to the present invention may have various embodiments also in respect of its layer configuration. Accordingly, the pack 1A for the nose as shown in FIGS. 1A and 1B is formed in a laminate structure constituted of the moisture-permeable holding member 20 formed of a nonwoven fabric of double-layer structure comprised of a water-repellent layer 21 and a hydrophilic layer 22, the cosmetic material 30 held in the moisture-permeable holding member 20 and also present as a sole layer on the hydrophilic layer 22, and the release film 40 provided on the surface of the cosmetic material 30. Besides, e.g., as shown in FIG. 4, a moisture-impermeable filmy base material 23 may be used as the holding member 20, an adhesive layer 31 comprised of the cosmetic material may be laminated to this filmy base material 23 and the release film 40 may be laminated thereon to form an adhesive tape type product.

Thus, the pack for the nose according to the present invention may have various layer configuration. In particular, it may preferably be made up in the following way: As shown in FIG. 1B, the holding member 20 comprises the multi-layer type moisture-permeable holding member 20 having the water-repellent layer 21 and the hydrophilic layer 22, where the cosmetic material 30 is held in at least the hydrophilic layer 22 of the moisture-permeable holding member 20 and the water-repellent layer 21 forms one surface of the sheet-like pack. Also, the release film 40 may preferably be provided on the surface of the cosmetic material 30 on the side of the hydrophilic layer 22. Since the cosmetic material 30 is held in the holding member in this way, the pack can be prevented from being torn off or remaining unpeeled when the pack for the nose is applied to the skin and thereafter peeled. Since also the holding member is moisture-permeable, the cosmetic material 30 can be formed into a film at a higher rate. Moreover, since this moisture-permeable holding member 20 is of the multi-layer type having the water-repellent layer 21 and the hydrophilic layer 22, the cosmetic material 30 can be made not to come through the surface of the water-repellent layer 21 while making the hydrophilic layer 22 hold the cosmetic material 30, thus the pack can be not sticky and the hands can be prevented from being stained with the cosmetic material 30.

In the present invention, there are no particular limitations on the individual materials for constituting the sheet-like pack, such as those for the moisture-impermeable filmy base material 23 or moisture-permeable holding member 20, those for the water-repellent layer 21 and hydrophilic layer 22 constituting the moisture-permeable holding member 20, and those for the cosmetic material 30 and release film 40. For example, the water-repellent layer 21 and hydrophilic layer 22 constituting the moisture-permeable holding member 20 may be formed of various types of nonwoven fabric, cloth, or a laminate prepared by laminating or bonding any of these to a film. In particular, in view of productivity and cost, nonwoven fabric is preferred. It is also possible to use a material obtained by subjecting such a nonwoven fabric to water-repellent treatment or hydrophilic treatment.

As the cosmetic material 30, various film-forming cosmetic materials conventionally used in peel-off type packs and cosmetic materials capable of forming a water-containing gel as used in cataplasms may be used. It may also be used in the form of a paste already containing sufficient water, or may be used in a dry state at the beginning while supplying water content when actually used. Also, in the case when as shown in FIG. 4 the cosmetic material is formed into the adhesive layer 31 and this is laminated to the filmy base material 23 to provide the pack for the nose in the form of an adhesive tape, the adhesive layer 31 comprised of the cosmetic material may be formed of a material that can be stuck to the nose as it is without feeding water when used.

The cosmetic material 30 may also be made up as a cosmetic material used as any of a moisture-retentive cosmetic material, a sebum-absorptive cosmetic material and a keratotic plug removable cosmetic material, and may contain components in accordance with the uses. In particular, a pack for the nose which is very suitable as a pack for pores of the skin, used to remove keratotic plugs of the nose, can be obtained when the keratotic plug removable cosmetic material is used.

In such an instance, as the keratotic plug removable cosmetic material, in view of advantages that a film with a high film strength can be formed, the keratotic plugs in the skin can be gripped into the film and the film can be removed by peeling, it is preferable to use as a film forming agent a polymeric compound having an anionic, cationic or amphoteric salt-forming group as disclosed in the claims in Japanese Patent Application Laid-open No. 5-97627, stated more specifically, a salt-forming group such as a carboxyl group, a sulfonic acid residual group, a sulfuric acid residual group, a phosphoric acid residual group, a nitric acid residual group, an amino group and an ammonium group. In particular, those containing polymethacryloyloxyethyltrimethylammonium chloride is preferred.

As the release film 40, for example, polyester, polypropylene, polyethylene, nylon or the like may be used.

Figure 5:
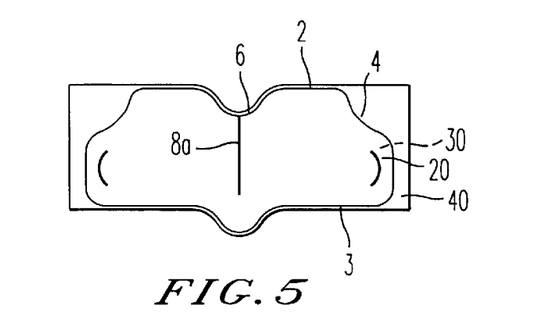
FIG. 5 is a plan view of the pack for the nose according to the present invention.
Figure 6:
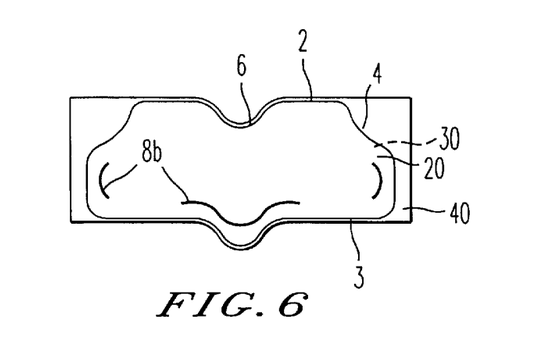
FIG. 6 is a plan view of the pack for the nose according to the present invention.

In the present invention, any mark may be optionally printed on the outer surface of the holding member. In this instance, what is printed may be, e.g., as shown in FIG. 5, a line pattern 8a that guides the position of the ridge of the nose when applied, or, as shown in FIG. 6, a pattern 8b of the nose. This enables much easier registration of the pack for the nose when it is applied to the nose.

INDUSTRIAL APPLICABILITY

According to the pack for the nose of the present invention, the pack can readily fit with the nose of various shapes, inclusive of the tip of the nose, and also the yield of products can be improved when manufactured in a conveyor system. Also, when, in the pack for the nose according to the present invention, the holding member is formed of a multi-layer type moisture-permeable holding member having a water-repellent layer and a hydrophilic layer and the keratotic plug removable cosmetic material is used as the cosmetic material, the pack can be especially useful as a pack for pores of the skin.

What is claimed is:

1. A sheet pack for the nose, comprising:
   i) a holding member layer; and
   ii) a cosmetic material layer,
   wherein said sheet pack comprises an upper edge and a lower edge,
   said upper edge of said pack comprising a portion receding from adjacent straight linear portions formed at a middle of said pack, and
   said lower edge of said pack comprising a portion projecting from adjacent straight linear portions formed at the middle of said pack,
   wherein said receding portion and said projecting portion are fittable with each other.

2. The pack for the nose according to claims, wherein said pack has a height of about 30 to 50 mm: and
   the receding portion or projecting portion has an outer shape with a width of from 5 mm to 50 mm and a height of from 3 mm to 30 mm.

3. The pack for the nose according to claim 2, wherein the receding portion or projecting portion is formed of an arc having a curvature radius of from 3 mm to 40 mm.

4. The pack for the nose according to claim 1, which is held on a release film.

5. The pack for the nose according to claim 1, wherein said holding member layer is moisture-permeable.

6. The pack for the nose according to claims 5, wherein said moisture-permeable holding member layer comprises a multi-layer moisture-permeable holding member having a water-repellent layer and a hydrophilic layer, and a cosmetic material of said cosmetic material layer is held in at least the hydrophilic layer; and said water-repellent layer forms one surface of said sheet pack.

7. The pack for the nose according to claim 6, wherein said water-repellent layer and hydrophilic layer of said multi-layer moisture-permeable holding member layer each comprise a nonwoven fabric, and said cosmetic material comprises a keratotic plug removable cosmetic material.

8. The pack for the nose according to claim 7, wherein said keratotic plug removable cosmetic material contains a polymeric compound having a salt-forming group selected from a carboxyl group, a sulfonic acid residual group, a sulfuric acid residual group, a phosphoric acid residual group, a nitric acid residual group, an amino group and an ammonium group.

9. The pack for the nose according to claim 8, wherein said keratotic plug-removable cosmetic material contains polymethacryloyloxyethyltrimethylammonium chloride.

10. A method of forming sheet packs for the nose, each comprising:
    i) a holding member layer; and
    ii) a cosmetic material layer,
    wherein each sheet pack comprises an upper edge and a lower edge,
    said upper edge of said pack comprising a portion receding from adjacent straight linear portions formed at a middle of said pack, and
    said lower edge of said pack comprising a portion projecting from adjacent straight linear portions formed at the middle of said pack,
    said method comprising of cutting a sheet, simultaneously forming said projecting portion of a lower edge of a pack and forming said receding portion of an upper edge of a vertically adjacent pack.

11. A sheet comprising a plurality of sheet packs for the nose, each comprising:

i) a holding member layer; and ii) a cosmetic material layer, wherein each sheet pack comprises an upper edge and a lower edge, said upper edge of said pack comprising a portion receding from adjacent straight linear portions formed at a middle of said pack, and said lower edge of said pack comprising a portion projecting from adjacent straight linear portions formed at the middle of said pack, wherein a projecting portion of a lower edge of a pack and a portion receding portion of an upper edge of a vertically adjacent pack are fittable with each other.

* * * * *